US008247340B2

(12) United States Patent
Johnson et al.

(10) Patent No.: US 8,247,340 B2
(45) Date of Patent: Aug. 21, 2012

(54) CATALYST FORMULATION FOR HYDROGENATION

(75) Inventors: Marvin M. Johnson, Bartlesville, OK (US); Edward R. Peterson, Pearland, TX (US); Sean C. Gattis, Sugar Land, TX (US)

(73) Assignee: Synfuels International, Inc., Dallas, TX (US)

( * ) Notice: Subject to any disclaimer, the term of this patent is extended or adjusted under 35 U.S.C. 154(b) by 0 days.

(21) Appl. No.: 13/045,346

(22) Filed: Mar. 10, 2011

(65) Prior Publication Data

US 2011/0217781 A1 Sep. 8, 2011

Related U.S. Application Data

(62) Division of application No. 10/727,919, filed on Dec. 4, 2003, now Pat. No. 7,919,431.

(60) Provisional application No. 60/499,839, filed on Sep. 3, 2003, provisional application No. 60/499,842, filed on Sep. 3, 2003.

(51) Int. Cl.
*B01J 23/00* (2006.01)
*B01J 21/00* (2006.01)
*B01J 31/00* (2006.01)
*B01J 37/00* (2006.01)

(52) U.S. Cl. ........ 502/104; 502/324; 502/327; 502/329; 502/332; 502/333; 502/339; 502/341; 502/342; 502/355; 502/415; 502/439

(58) Field of Classification Search ................. 502/104, 502/324, 327, 329, 332, 333, 339, 341, 342, 502/355, 415, 439

See application file for complete search history.

(56) References Cited

U.S. PATENT DOCUMENTS

| | | |
|---|---|---|
| 2,091,114 A | 8/1937 | Daudt |
| 2,525,210 A | 10/1950 | Camp |
| 3,147,229 A | 9/1964 | Hinlicky et al. |
| 3,342,891 A | 9/1967 | Poons et al. |
| 3,541,178 A | 11/1970 | Nettesheim |
| 3,674,886 A | 7/1972 | Komatsu et al. |
| 3,755,488 A | 8/1973 | Johnson et al. |
| 3,842,137 A | 10/1974 | Libers et al. |
| 3,867,309 A | 2/1975 | Oleck et al. |
| 3,894,967 A | 7/1975 | Koepernik et al. |
| 3,912,789 A | 10/1975 | Frevel et al. |
| 3,962,285 A | 6/1976 | Cusumano |
| 4,001,344 A | 1/1977 | Hoffmann et al. |
| 4,112,007 A | 9/1978 | Sanfilippo et al. |
| 4,126,645 A | 11/1978 | Collins |
| 4,128,595 A | 12/1978 | Montgomery |
| 4,137,267 A | 1/1979 | Reid et al. |
| 4,243,516 A | 1/1981 | Martinon et al. |
| 4,277,313 A | 7/1981 | Mehra et al. |
| 4,323,482 A | 4/1982 | Stiles et al. |
| 4,337,329 A | 6/1982 | Kubo et al. |
| 4,404,124 A | 9/1983 | Johnson et al. |
| 4,469,907 A | 9/1984 | Araki et al. |
| 4,484,015 A | 11/1984 | Johnson et al. |
| 4,517,395 A | 5/1985 | Obenaus et al. |
| 4,547,600 A | 10/1985 | Cosyns et al. |
| 4,705,906 A | 11/1987 | Brophy et al. |
| 4,812,435 A | 3/1989 | Baird, Jr. |
| 4,906,800 A | 3/1990 | Henry et al. |
| 4,973,786 A | 11/1990 | Karra |
| 5,059,732 A | 10/1991 | Cosyns et al. |
| 5,128,306 A | 7/1992 | Dettling et al. |
| 5,176,887 A | 1/1993 | Subramanian et al. |
| 5,227,553 A | 7/1993 | Polanek et al. |
| 5,356,851 A | 10/1994 | Sarrazin et al. |
| 5,364,998 A | 11/1994 | Sarrazin et al. |
| 5,414,170 A | 5/1995 | McCue et al. |
| 5,482,615 A | 1/1996 | Meitzner et al. |
| 5,504,268 A | 4/1996 | van der Aalst et al. |
| 5,587,348 A | 12/1996 | Brown et al. |
| 5,589,600 A | 12/1996 | Fischer et al. |
| 5,696,293 A | 12/1997 | Phillips et al. |
| 5,847,250 A | 12/1998 | Flick et al. |
| 5,856,262 A | 1/1999 | Flick et al. |
| 5,866,734 A | 2/1999 | Flick et al. |
| 5,925,239 A | 7/1999 | Klein et al. |
| 6,015,933 A | 1/2000 | Abrevaya et al. |
| 6,093,670 A | 7/2000 | Brown |
| 6,103,106 A | 8/2000 | McVicker et al. |
| 6,127,310 A | 10/2000 | Brown et al. |
| 6,130,260 A | 10/2000 | Hall et al. |
| 6,204,218 B1 * | 3/2001 | Flick et al. ..................... 502/243 |
| 6,221,240 B1 | 4/2001 | Klein et al. |

(Continued)

FOREIGN PATENT DOCUMENTS

DE 871804 2/1958

(Continued)

OTHER PUBLICATIONS

EPO Search Report dated Feb. 25, 2008, for EPO Application No. 03796762.7, 6 pages.
A. Malek and S. Farooq, Hydrogen Purification from Refinery Fuel Gas by Pressure Swing Adsorption, AIChE Journal, Sep. 1998, vol. 44, No. 9, pp. 1985-1992.
International Search Report for PCT/US2003/038871 dated Dec. 6, 2004, 2 pages.
International Search Report for PCT/US2004/015293 dated Apr. 18, 2005, 2 pages.
Gulf Cooperation Council First Examination Report mailed Mar. 12, 2008, pp. 1-7.

(Continued)

*Primary Examiner* — Cam N. Nguyen
(74) *Attorney, Agent, or Firm* — Timothy S. Westby; Porter Hedges LLP

(57) ABSTRACT

A composition and method for preparation of a catalyst for the liquid phase selective hydrogenation of alkynes to alkenes with high selectivity to alkenes relative to alkanes, high alkyne conversion, and sustained catalytic activity comprising a Group VIII metal and a Group IB, Group IIB, Group IIIA, and/or Group VIIB promoter on a particulate support.

26 Claims, No Drawings

U.S. PATENT DOCUMENTS

| | | |
|---|---|---|
| 6,255,548 B1 | 7/2001 | Didillon et al. |
| 6,281,160 B1 | 8/2001 | Basset et al. |
| 6,315,892 B1 | 11/2001 | Le Peltier et al. |
| 6,323,247 B1 | 11/2001 | Hall et al. |
| 6,340,429 B1 | 1/2002 | Minkkinen et al. |
| 6,350,717 B1 | 2/2002 | Frenzel et al. |
| 6,358,399 B1 | 3/2002 | Minkkinen et al. |
| 6,365,790 B2 | 4/2002 | Reimer et al. |
| 6,395,952 B1 | 5/2002 | Barchas |
| 6,459,008 B1 | 10/2002 | Dai et al. |
| 6,465,391 B1 | 10/2002 | Cheung et al. |
| 6,509,292 B1 | 1/2003 | Blankenship et al. |
| 6,528,453 B2 * | 3/2003 | Baker et al. ................. 502/325 |
| 6,576,588 B2 | 6/2003 | Ryu et al. |
| 6,578,378 B2 | 6/2003 | Kaiser et al. |
| 6,602,920 B2 | 8/2003 | Hall et al. |
| 2002/0000085 A1 | 1/2002 | Hall et al. |
| 2002/0068843 A1 | 6/2002 | Dai et al. |
| 2003/0105378 A1 | 6/2003 | Satek et al. |
| 2003/0225305 A1 | 12/2003 | Kaminski |
| 2004/0002553 A1 | 1/2004 | Hall et al. |

FOREIGN PATENT DOCUMENTS

| | | |
|---|---|---|
| DE | 2619660 | 11/1976 |
| EP | 0225185 | 6/1987 |
| EP | 564328 | 6/1993 |
| EP | 564329 | 6/1993 |
| EP | 1358935 | 11/2003 |
| FR | 2091114 | 1/1972 |
| FR | 2525210 | 10/1983 |
| WO | 9837966 | 9/1998 |

OTHER PUBLICATIONS

Gulf Cooperation Council Search Report mailed Apr. 10, 2008, pp. 1-5.
Gulf Cooperation Council Second Examination Report mailed Aug. 24, 2009, pp. 1-6.
Gulf Cooperation Council Third Examination Report mailed Oct. 17, 2010, pp. 1-6.
European Patent Office Examination Report mailed Dec. 22, 2009.
EPO Search Report dated Mar. 23, 2012, for corresponding EP Application No. 11010121.9, 10 pages.
EPO Search Report dated Mar. 28, 2012, for corresponding EP Application No. 11010119.3, 8 pages.

* cited by examiner

CATALYST FORMULATION FOR HYDROGENATION

CROSS-REFERENCE TO RELATED APPLICATIONS

This application is a divisional application of U.S. patent application Ser. No. 10/727,919 (now U.S. Pat. No. 7,919,431), filed Dec. 4, 2003, which claims the benefit under 35 U.S.C. §119(e) of U.S. Provisional Patent Application No. 60/499,839, filed Sep. 3, 2003, and U.S. Provisional Patent Application No. 60/499,842, filed Sep. 3, 2003. The disclosure of each of said applications is hereby incorporated herein by reference.

STATEMENT REGARDING FEDERALLY SPONSORED RESEARCH OR DEVELOPMENT

Not Applicable.

BACKGROUND OF THE INVENTION

1. Field of the Invention

This invention relates generally to novel catalysts for the selective hydrogenation of unsaturated compounds. In particular, the catalyst of the invention preferably contains a Group VIII (using the CAS naming convention) metal and a promoter element, which may be chosen from the groups that contain silver, gallium and indium, manganese, and zinc.

2. Description of the Related Art

Hydrogenation of alkynes and/or multifunctional alkenes to compounds containing only one alkene group is an important industrial process and is discussed widely in the patent literature. Acetylene, the simplest alkyne, occurs in many processes as a main product or by-product which is thereafter converted to ethylene or ethane by hydrogenation. Thermal cracking of ethane can be caused to produce mostly ethylene, but a minor undesired product is acetylene. Pyrolysis of simple alkanes or mixtures containing primarily alkanes and partial oxidation of simple alkanes or mixtures containing primarily alkanes can be made to produce various blends that contain as principal products both alkenes and alkynes. Products in lower abundance will often include diolefins, compounds containing both yne and ene functionalities, polyenes, and other unsaturated moieties. Most commonly the desired products are the singly dehydrated compounds containing a single ene functionality. Thus, it is desirable to convert the alkynes to alkenes, but not convert the desired alkenes further to alkanes. Reactions of alkenes are generally more controllable than those of alkynes and diolefins, which tend to create oligomers and undesirable polyfunctional compounds.

The hydrogenation step is normally carried out on the primary gas produced in the cracking or pyrolysis reaction of natural gas and low molecular weight hydrocarbons, which includes all the initial gas products, also known as "front-end" hydrogenation, or subsequent to fractionation of the gas components, wherein the only stream subjected to hydrogenation is enriched in the highly unsaturated compounds, also known as "tail-end" hydrogenation. The advantage of primary gas hydrogenation is generally an abundance of the hydrogen required for hydrogenation. However, the excess available hydrogen in front-end hydrogenation can result in "run-away" reactivity wherein conversion of alkenes to alkanes reduces the value of the product. Fractionation reduces the available hydrogen but polymer formation is common, the effect of which is to shorten the useful life of the catalyst.

There are numerous examples of gas-phase hydrogenation of alkynes. For example, U.S. Pat. No. 6,127,310 by Brown, et al. teaches that the selective hydrogenation of alkynes, which frequently are present in small amounts in alkene-containing streams (e.g., acetylene contained in ethylene streams from thermal alkane crackers), is commercially carried out in the presence of supported palladium catalysts in the gas-phase.

In the case of the selective hydrogenation of acetylene to ethylene, preferably an alumina-supported palladium/silver catalyst in accordance with the disclosure in U.S. Pat. No. 4,404,124 and its division U.S. Pat. No. 4,484,015 is used. The operating temperature for this hydrogenation process is selected such that essentially all acetylene is hydrogenated to ethylene (and thus removed from the feed stream) while only an insignificant amount of ethylene is hydrogenated to ethane. Proper temperature selection and control results in minimization of ethylene losses and allows one to avoid a runaway reaction, which is difficult to control.

U.S. Pat. No. 5,856,262 describes use of a palladium catalyst supported on potassium doped silica wherein acetylene ranging in concentration from 0.01% to 5% in blends of ethylene and ethane is converted to ethylene in the gas-phase. U.S. Pat. No. 6,350,717 describes use of a palladium-silver supported catalyst to hydrogenate acetylene to ethylene in the gas-phase. The acetylene is present at levels of 1% in a stream of ethylene. U.S. Pat. No. 6,509,292 describes use of a palladium-gold catalyst wherein acetylene contained in a stream of principally ethylene, hydrogen, methane, ethane and minor amounts of carbon monoxide converts acetylene to ethylene in the gas-phase.

U.S. Pat. No. 6,395,952 describes recovery of olefins from a cracked gas stream using metallic salts and ligands. The cracked gas stream is hydrogenated prior to scrubbing to remove acetylene from the stream.

U.S. Pat. No. 5,587,348 describes hydrogenation of $C_2$ to $C_{10}$ alkynes contained in comparable streams of like alkenes over a supported palladium catalyst containing fluoride and at least one alkali metal. Examples show hydrogenation of low concentrations of acetylene, below 1%, being converted to ethylene in a gas principally comprised of methane and ethylene at 200 psig and 130° F. and 180° F. Care was taken to avoid heating the gas to a runaway temperature, wherein at least 4.5% of the ethylene would be converted to ethane and the temperature would become uncontrollable, which varied from about 70° F. to 100° F. above the minimum temperature that would reduce the acetylene concentration to acceptable levels.

U.S. Pat. No. 6,578,378 describes a complex process for purification of ethylene produced from pyrolysis of hydrocarbons wherein the hydrogenation follows the tail-end hydrogenation technique. At the top of the de-ethanizer the vapor of the column distillate is treated directly in an acetylene hydrogenation reactor, the effluent containing virtually no acetylene being separated by a distillation column called a de-methanizer, into ethylene- and ethane-enriched tail product. The vapor containing acetylene is exposed to selective hydrogenation to reduce acetylene content of the principally ethylene gas or treated with solvent to remove it and preserve it as a separate product. In all cases the acetylene content of the pyrolysis gas contained less than 1.5 mol % acetylene.

Hydrogenation is also known to occur in the liquid phase where the fluids are easily conveyed or transported as liquids under reasonable temperature and pressure. Naphtha cracking produces significant quantities of $C_4$ and $C_5$ unsaturated compounds, with 1,3 butadiene and 1-butene generally having the greatest commercial value.

U.S. Pat. No. 6,015,933 describes a process in which polymer by-products from the steam cracking of naphtha to butadiene are removed. Acetylenes in the liquid hydrocarbon stream are selectively hydrogenated in a reactor to produce a reactor product containing at least hydrogen, butadiene, and polymer by-products having from about 8 to about 36 carbon atoms, and typically containing butenes and butanes. The acetylenic compounds are primarily vinyl acetylene, ethylacetylene, and methylacetylene. These acetylene group-containing molecules are converted to 1,3 butadiene, 1-butene, and propylene, but can react further with butadiene to form polymeric by-products. The reaction is carried out in the liquid phase with butadiene as the carrier. The undesirable feature of this process is that the carrier reacts with the products of the hydrogenation reaction, necessitating the removal of the polymeric by-products described.

U.S. Pat. No. 5,227,553 describes a dual bed process for hydrogenating butadiene to butenes. This improvement is said to increase selectivity in streams containing high concentrations of butadiene while reducing the isomerization of butene-1 to butene-2, and nearly eliminating the hydrogenation of isobutene to isobutane as well as oligomerization.

U.S. Pat. No. 4,547,600 discloses the need for more silver than previously thought necessary in the hydrogenation of acetylenic compounds that are found in butadiene as a result of steam cracking. The reaction is performed in the liquid phase where the product is the carrier.

U.S. Pat. No. 3,541,178 reports a reduction in the loss of butadiene along with nearly complete reduction of acetylenic compounds by restricting the flow of hydrogen to no more than 80% to 90% of saturation in the hydrocarbon stream. This reduces the potential for polymerization of the vinylacetylenes, as there is no hydrogen remaining in the reaction stream at the end of the reaction. The undesirable aspect of this reduced hydrogen content however, is that the concentration of the hydrogen in the reactor is reduced, which decreases the reaction rate.

U.S. Pat. No. 3,842,137 also teaches a reduction in the loss of butadiene to butene along with nearly complete conversion of vinylacetylene to butadiene, through the use of an inert diluent gas for the hydrogen. The hydrogen-containing gas includes no more than 25% hydrogen. The reaction takes place in the liquid phase, between a temperature of 40° F. and 175° F., and at a pressure of 80 to 200 psig. Again however, an undesirable aspect of using a diluent is that concentration of the hydrogen in the reactor is reduced, which decreases the reaction rate.

U.S. Pat. No. 4,469,907 teaches high conversions of multiply unsaturated hydrocarbons to singly unsaturated hydrocarbons without subsequent isomerization, by staging the insertion of hydrogen into one or more reactors in series. An undesirable aspect of using several reactors however, is the increased complexity of the process, resulting in increased cost and more complicated process control.

There are several examples where non-linear and/or non-hydrocarbon compounds are hydrogenated in the liquid phase. For example, U.S. Pat. No. 5,696,293 describes liquid phase hydrogenation and amination of polyols, carried out at pressures below 20 MPa using a supported ruthenium catalyst and containing another metal from Groups VIA, VIIA, and VIII. A ruthenium-palladium or singly palladium catalyst is listed in the examples. An undesirable feature of this process is the need to filter the fine and expensive catalyst out of the product. Catalyst losses are potentially very costly.

U.S. Pat. No. 5,589,600 discloses hydrogenation of benzene to cyclohexene using ruthenium-nickel catalysts in the presence of water, which is purported to improve selectivity.

U.S. Pat. No. 5,504,268 discloses hydrogenation of aromatic acetylenic compounds that are impurities in vinyl aromatic compounds, over a supported palladium catalyst. The purported improvement is obtained via reduction of the hydrogen concentration by using a gas phase diluent such as nitrogen or methane. As previously noted, an undesirable aspect of using a diluent however, is the reduction in the concentration of hydrogen in the reactor and corresponding decrease in the reaction rate.

Carbon monoxide is known to enhance hydrogenation selectivity. It is added to a stream that has been thermally cracked or pyrolyzed to reduce the hydrogenation of the ene functional groups. U.S. Pat. No. 6,365,790 describes an approach to selective hydrogenation of $C_{10}$ to $C_{30}$ alkynes to their respective alkenes in the liquid phase, by careful addition of a compound that decomposes to form CO. An undesirable aspect of using an additive is that the additive must later be removed from the product in diminished form.

U.S. Pat. No. 4,517,395 indicates that CO and $H_2$ added to a liquid phase of $C_{3+}$ multi-ene or mono-yne hydrocarbons, dispersed in the single-ene containing hydrocarbons, results in improved conversion due to better selectivity. The emphasis is on maintaining sufficient pressure to hold the CO and $H_2$ in the liquid phase rather than dispersed as a heterogeneous phase. Notably, water is added to reduce the amount of CO required as well as to reduce the temperature required.

U.S. Pat. No. 4,705,906 presents a catalyst formulation wherein acetylene is converted by hydrogenation to ethylene, in the presence of CO in concentrations greater than 1 vol % in a temperature range between 100° C. and 500° C. The catalyst is a zinc oxide or sulphide, which may incorporate chromium, thorium, or gallium oxide. Zinc oxide and zinc sulphide were reportedly chosen for the reason that, although palladium catalysts are reasonably tolerant of the usual organic impurities which act solely as activity moderators, palladium catalysts are poisoned at low temperatures by high concentrations of carbon monoxide, such as those associated with unsaturated hydrocarbon-containing products obtained by the partial combustion of gaseous paraffinic hydrocarbons. This is to be contrasted with their behavior at low carbon monoxide concentrations, typically at concentrations less than 1 vol %, at which moderation of catalytic activity is reported to enhance the selectivity of acetylene hydrogenation to ethylene. At high temperature, palladium catalysts are active even in the presence of carbon monoxide, but selectivity of acetylene hydrogenation to ethylene is drastically reduced by simultaneous hydrogenation of ethylene to ethane.

In U.S. Pat. No. 4,906,800, a Lindlar catalyst was used with a feed that contained no CO. The catalyst contained 5% palladium on a $CaCO_3$ support with about 3% lead as a promoter. After special treatment involving oxidation, reduction in CO, and finally a heat treatment step of the readily oxidized and reduced Lindlar catalyst, the treated catalyst showed improved selectivity at high conversion, but again at higher temperatures above 200° C. selectivity decreased significantly.

U.S. Pat. No. 5,847,250 describes a supported palladium catalyst employing a "promoter" from Groups 1 or 2 (in the New classification system; CAS Groups IA and IIA) and the palladium being supported on silica that has been pretreated to contain the promoter. The purported advantage is that no carbon monoxide is needed to provide increased selectivity because the selectivity-increasing effect of the carbon monoxide is strongly temperature dependent. Large temperature gradients in the catalyst bed therefore have an adverse effect on the selectivity when carbon monoxide is present. The reaction is performed in the gas phase in one or more beds with or without intermediate cooling or hydrogen gas addition. Acetylene content ranges from 0.01% to 5%. The reported selectivity ranges from 19 to 56%.

The use of liquid carriers has also been described in several patents for various reasons. For example, U.S. Pat. No. 4,137,267 describes the hydrogenation of alkyl aminoproprionitrile in the liquid phase, using hydrogen and ammonia as reactants over a supported catalyst and using an organic solvent. The solvent was selected to absorb excess heat by vaporizing at the process conditions, which is said to provide some temperature control. An undesirable aspect of employing a volatilizing solvent is the concomitant difficulty of employing this technique in a fixed catalyst bed.

U.S. Pat. No. 5,414,170 teaches selective hydrogenation of a stream from an olefin plant after operation of a depropanizer but prior to operation of a de-ethanizer or de-methanizer. The hydrogenation is performed on the mixed-phase propane rich ethylene stream, as well as subsequently on the vapor product. A method is described by which the acetylenes in the front end of an olefin plant process stream are hydrogenated in the presence of a liquid hydrocarbon. The propane liquids, initially separated out of the inlet process stream, are used later to cool and wash the product of the acetylene hydrogenation reactor by adding them to the acetylene-containing stream during hydrogenation. An undesirable aspect of this process is the need to fractionate the propane from the small amount of ethylene produced.

U.S. Pat. No. 5,059,732 discloses a process to hydrogenate effluent from a steam cracker containing ethylene, acetylene, propylene, propyne, propadiene, and butadiene, with hydrogen in the presence of a palladium or other noble metal catalyst by use of a gasoline cut as an inert carrier. The rationale for improved catalyst life is that the aromatic content of the gasoline carrier prevents plating out of the diolefins on the catalyst, which can otherwise polymerize and form gums that obstruct the other reactive components from getting to the catalyst surface. An undesirable aspect of this process however, is the need to fractionate the heavier hydrocarbon fraction from the small amount of ethylene produced, although this is not as serious a problem as when propane is used as the carrier.

Several patents disclose the use of solvents to separate the acetylenic fraction of a fluid stream from the other components. It is well known that dimethylformamide (DMF) and n-methyl-2-pyrrolidone (NMP) are good liquid absorbents for acetylene. Likewise, it is well known that DMF, furfural, ethylacetate, tetrahydrofuran (THF), ethanol, butanol, cyclohexanol, and acetonitrile are useful absorbents for 1,3-butadiene.

French Pat. No. 2,525,210 describes a method for the purification of a stream containing mostly ethylene with a smaller amount of acetylene contaminant, wherein the acetylene is not converted to ethane. The basic concept is to hydrogenate a gas stream short of complete conversion, leaving some acetylene in the gas stream, then to absorb the acetylene in a solvent that extracts the acetylene from the ethylene stream. This extracted acetylene is separated from the solvent and recycled to the ethylene stream for hydrogenation. This is said to increase conversion to ethylene. An undesirable aspect of this process is the need to control the hydrogenation significantly below complete conversion.

U.S. Pat. No. 4,277,313 focuses on the purification of a $C_4$ stream containing acetylenic compounds by hydrogenation of the acetylenic compounds followed by downstream separation. The hydrogenation step is carried out in the liquid phase after the hydrocarbon has been separated from the absorbing solvent. It is said to be important to remove the acetylenic compounds prior to polymerization since they can form explosive metal acetylides and will cause the polymer to be off-spec. Suitable inert solvents for this process purportedly include: dimethylformamide (DMF), furfural, ethylacetate, tetrahydrofuran (THF), ethanol, butanol, cyclohexanol, and particularly acetonitrile.

U.S. Pat. No. 3,342,891 describes fractionating a stream of $C_4$ and $C_5$ alkadienes into two streams, where one stream is reduced in vinyl acetylenes and the second stream is enriched in vinyl acetylenes. DMSO was used to separate the vinylacetylene from the enriched stream. The DMSO that contains the vinylacetylene was stripped with nitrogen to concentrate the vinylacetylene, which was subsequently hydrogenated in the gas phase. Unconverted vinyl acetylene in the effluent is recycled back to the feed of the fractionation column.

In some examples, the use of a liquid carrier or solvent is disclosed in which the liquid carrier or solvent is present during the hydrogenation step. U.S. Pat. No. 4,128,595 for example, teaches a process wherein gaseous acetylene or acetylene group containing compounds are contacted with hydrogen via an inert saturated liquid hydrocarbon stream with hydrogenation occurring over a typical Group VIII metal supported on a catalyst medium. Examples of inert saturated hydrocarbons include various hexanes, decanes and decalin. The process requires the acetylene containing compound and saturated hydrocarbon solvent be fed co-currently into the top of a trickle bed reactor because the solubility of the acetylene containing compound in the saturated hydrocarbon solvent is poor at reaction conditions. An undesirable aspect of this process is the poor solubility of the hydrocarbon solvent toward acetylene. This patent teaches that rapid catalyst deactivation can occur with polar solvents. Dimethylformamide (DMF) was used as an absorbent for ethylene and the polar solvent during hydrogenation. The result indicated rapid catalyst deactivation with conversion dropping from 100% to 50% over a period of 17 hours. Accordingly, there is substantial need for a practicable liquid phase hydrogenation process, using non-hydrocarbon solvents, with supported palladium-based catalysts, if these could be developed with sufficient activity and selectivity.

Combinations of Group VIII catalysts with Group IIIA metals are found in the art for various applications. French Pat. No. 2,091,114 and U.S. Pat. No. 6,315,892 describe a catalyst and process respectively in which a palladium/indium supported catalyst was used to dehydrogenate and reform petroleum liquids. This patent discloses the use of a palladium/indium supported catalyst for hydrogenation, which is the reverse chemical reaction.

U.S. Pat. No. 5,356,851, EP 564,328, and EP 564,329 describe palladium/gallium catalyst and teach that the group IIIA metal must be deposited on the support before the group VIII metal to achieve superior activity and selectivity for hydrogenation. An undesirable aspect of this method is that the catalyst cannot be formulated as an existing Group VIII catalyst subsequently modified to impart the group IIIA promoter functionality.

U.S. Pat. No. 6,465,391 describes a catalyst that contains palladium, silver, and an alkaline metal fluoride compound, wherein the metal is chosen from the group of antimony, phosphorus, boron, aluminum, gallium, indium, thallium, and arsenic, for hydrogenation of acetylene in a gas stream that contains about 1.25% acetylene in ethylene. However, this catalyst formulation exhibits a selectivity to ethylene of less than 80% in all reported cases.

U.S. Pat. No. 5,866,734 describes a catalyst formed from sputtering metals onto a metal mesh support. Specific examples for hydrogenation include palladium, palladium/silver, and palladium/magnesium on wire mesh supports. Some of the undesirable aspects of using wire or foil meshes are that they are difficult and expensive to manufacture, and generally have limited regeneration temperatures and therefore uses.

U.S. Pat. No. 6,255,548 and U.S. Pat. No. 6,281,160 describe a process for hydrogenation and a process to manufacture a catalyst respectively, whereby a Group VIII metal and metal M, selected from germanium, tin, lead, rhenium, gallium, indium, gold, silver, and thallium are deposited on a support for the purpose of the hydrogenation of acetylenic compounds or diolefins. The deposition of the metal M is accomplished by solubilizing an organometalic compound of M that is soluble in water. An example is presented for a palladium/tin catalyst formed using tributyltin acetate. The resulting catalyst is used to convert isoprene in heptane to n-methylbutene with 98% selectivity.

U.S. Pat. No. 4,337,329 relates to a supported catalyst on which palladium and a metal from groups IA, IIA, IIIA, IVA, VA, VIA, as well as germanium and antimony are deposited, for hydrogenating carbon-carbon double bonds of a conjugated diene polymer. An undesirable aspect of using a supported catalyst to hydrogenate a polymer, even a low molecular weight polymer, is the difficulty of recovering the catalyst once the hydrogenation is complete.

U.S. Pat. No. 4,323,482 discloses formulation of a catalyst from a metal oxide mixture where one component is reducible and the other is not reducible under selected process conditions. The resulting catalyst has reduced crystallite character which enhances activity. An undesirable aspect of this catalyst preparation is that subsequent processing or regeneration at high temperatures in a reducing atmosphere will tend to cause the catalyst crystallinity to continuously increase.

As is apparent, an efficient, practicable process for liquid-phase selective hydrogenation, using a catalyst with sufficient activity and selectivity, would be a substantial contribution to the art. It has now been found that significant improvements in the selectivity to ethylene can be obtained from the addition of promoters at high acetylene conversion in accordance with the present invention. Surprisingly, and contrary to the teachings of the conventional art relating to use of a polar solvent, such as dimethylformamide, a progressive decline in catalyst activity with time on stream is not observed with the present invention. Further, gallium and indium promoted catalysts of this invention exhibited satisfactory selectivity. Additionally, and contrary to the teachings of the prior art, excellent selectivity and activity results were obtained using a catalyst formed by first applying a Group VIII metal to the support and then subsequently applying a Group IIIA metal.

SUMMARY OF THE INVENTION

It is thus an object of the present invention to overcome the deficiencies of the prior art and to provide a catalyst for selective hydrogenation comprising, consisting essentially, or consisting of at least one Group VIII metal and at least one Group IB, IIB, VIIB, or IIIA (using the CAS classification system) metal, where the metals are deposited on a catalyst support.

The catalyst support may comprise a silica, an alumina, a silica-alumina, an aluminate, an alternate metal or alloy, a sintered or refractory oxide or carbide (including silicon carbide, tungsten carbide, and others known to those skilled in the art) or carbon. The aluminate may comprise mixed alkali metal, alkaline earth, zinc, or cadmium aluminate. The catalyst support is preferably an inorganic support and, more preferably, the catalyst support is an alumina support.

The Group VIII metal may be palladium, platinum, or nickel. The Group VIII metal is preferably palladium.

The Group IB metal may be copper, silver, or gold. The Group IB metal is preferably silver, gold, or a combination thereof. The Group VIIB metal may be manganese or rhenium. The Group VIIB metal is preferably manganese. The Group IIB metal is preferably zinc. The Group IIIA metal is preferably gallium, indium, or a combination thereof.

The present invention also provides a method for making a supported hydrogenation catalyst comprising: applying a Group VIII metal to a support to give a final concentration of from about 0.1% to about 1.0% by weight; applying a second metal to the first metal-coated support to give a final concentration of from about 0.05% to about 1.2% by weight; drying; calcining; and reducing such that the final catalyst exhibits a satisfactory conversion, selectivity, and sustained activity in liquid-phase selective hydrogenation.

The present invention also includes a catalyst as above wherein a supported Group VIII metal catalyst is obtained commercially and further prepared as described herein.

The present invention further provides a method for screening or evaluating the suitability of catalysts for selective hydrogenation, particularly for screening the catalysts on the basis of estimated or relative conversion, selectivity, and sustained activity. This method provides steps including (among others) applying one or more promoters to a supported Group VIII catalyst, preparing a reactant stream comprising acetylene in NMP, contacting the reactant stream and a hydrogen/carbon monoxide stream with both reference and test catalysts, and measuring product concentrations in steady-state liquid phase hydrogenation of acetylene, from which catalyst performance can be evaluated.

The present invention also includes a process for selective hydrogenation using the catalyst(s), catalyst preparation method(s), and catalyst screening method(s), all described in more detail herein.

DETAILED DESCRIPTION OF THE PREFERRED EMBODIMENTS

A preferred embodiment of the present invention provides a catalyst for selective hydrogenation comprising, consisting essentially, or consisting of at least one Group VIII metal and at least one Group IB, IIB, VIIB, or IIIA (CAS nomenclature) metal, which may be gallium, indium, silver, manganese, or zinc, where the metals are deposited on a catalyst support.

Another preferred embodiment of the present invention is a method for catalyst preparation, comprising: impregnating the support with a solution of a Group VIII metal compound or precursor, the metal concentration of the Group VIII metal compound or precursor preferably being chosen so that 0.01 to 10% of the Group VIII metal is fixed on the support; drying; calcining at 110° C. to 600° C.; reducing at 100° C. to 400° C.; impregnating with a solution of at least one of Group IB, IIB, VIIB, or IIIA metals or precursors, the metal or precursor concentration(s) preferably being chosen so that 0.01 to 10% of the at least one of Group IB, IIB, VIIB, or IIIA metals is fixed on the support; drying; calcining at 110° C. to 600° C.; and reducing at 100° C. to 400° C. The metals may preferably be applied to the support in any order.

In another preferred embodiment, the impregnating solution may comprise both the Group VIII metal compound or precursor and the at least one of Group IB, IIB, VIIB, or IIIA metals or precursors, such that the metals are preferably applied to the support together and at the same time. In this embodiment, the drying, calcining, and reducing steps may preferably be conducted once.

Another preferred embodiment of the present invention includes a catalyst for selective hydrogenation wherein a supported Group VIII metal catalyst is obtained commercially and further prepared as described herein preferably by wet impregnation with a promoter metal or metal precursor, although the promoter metal may be applied by any technique known in the art without departing from the scope of the invention.

The reducing gas is preferably hydrogen or a hydrogen-containing gas, as will be known to those of skill in the art, and may also contain carbon monoxide or a carbon monoxide-containing gas. Both the drying and calcining steps may take place in oxygen-containing or substantially oxygen-free environments.

The catalyst support is preferably an alumina, but may also be a silica, a silica-alumina, an aluminate, an alternate metal or alloy, a sintered or refractory oxide or carbide (including silicon carbide, tungsten carbide, and others known to those skilled in the art) or carbon. The aluminate may be mixed alkali metal, alkaline earth, zinc or cadmium aluminate. The Group VIII metal is preferably palladium but may also be platinum, or nickel. The Group IB metal may be copper, silver, or gold. The Group VIIB metal may be manganese or rhenium. The Group IIIA metal may be indium or gallium. The Group IIB metal may be zinc.

The Group IB or IIB metal concentration is preferably 0.01 to 10% by weight. The Group VIIB metal concentration is preferably 0.01 to 10% by weight. The Group IIIA metal concentration is preferably 0.01 to 10% by weight. The molar ratio of the group IB or IIB metal to group VIII metal may be from about 0.1 to about 10. The molar ratio of the group VIIB metal to group VIII metal may range from about 0.1 to about 10. The molar ratio of the group IIIA metal to group VIII metal may range from about 0.1 to about 10.

The present invention also includes catalysts in which the metal support may comprise a wire, wire mesh, powder, or shot composed of palladium, platinum, nickel, tungsten, tantalum, columbium, molybdenum, chromium, vanadium, titanium, iron, cobalt, carbon, and/or an alloy containing any or all of these elements. The sintered refractory oxide may be tantalum oxide, dysprosium oxide, titanium dioxide, ytterbium oxide, yttrium oxide, gadolinium oxide, and zirconium oxide.

In another preferred embodiment, the present invention further includes a method for screening or evaluating the suitability of catalysts for selective hydrogenation, particularly for screening the catalysts on the basis of estimated or relative conversion and selectivity.

In another preferred embodiment, the present invention further includes the application of catalysts as described herein to selective conversion of acetylenic compounds to ethylenic compounds comprising the charging of a feedstream containing the acetylenic compound or compounds to a single pass, continuous reactor containing the catalyst and operated at conditions conducive to hydrogenation. The acetylenic compound may be a gas and the reactor may be operated such that the fluid media in the reactor is in the gas or supercritical fluid phase form. The acetylenic compound may alternatively be a liquid and distributed as a component of a stream wholly or mostly in the gas state at reactor operating conditions such that the fluid media in the reactor is in a gas, supercritical, or mixed phase form. Further alternatively, the acetylenic compound may be a liquid and distributed as a component of a stream wholly or mostly in the liquid state at reactor operating conditions such that the fluid media in the reactor is in the liquid, supercritical, or mixed phase form. Also, the acetylenic compound may be a gas at reactor operating conditions and distributed as a component of a stream wholly or mostly in the liquid state such that the fluid media in the reactor is in a liquid, supercritical, or mixed phase form.

In another preferred embodiment, the present invention provides a process for the use of the inventive catalysts as described in our co-filed application Ser. No. 10/728,310 (now U.S. Pat. No. 7,045,670), entitled "Process for Liquid Phase Hydrogenation" by Marvin M. Johnson, Edward R. Peterson, and Sean C. Gattis, hereby incorporated by reference herein in its entirety.

The acetylenic compound will typically be absorbed in a non-hydrocarbon solvent, and the non-hydrocarbon solvent may be a polar solvent including, but not limited to: n-methyl-2-pyrrolidone (NMP), dimethylformamide (DMF), acetone, tetrahydrofuran (THF), dimethylsulfoxide (DMSO), and monomethylamine (MMA).

To more clearly illustrate the present invention, several examples are presented below. These examples are intended to be illustrative and no limitations to the present invention should be drawn or inferred from the examples presented herein.

EXAMPLES

Catalyst Preparation

A number of experimental catalysts were prepared by incipient wetness impregnation of a commercially available "skin" catalyst (also known in the art as "rim" or "eggshell" catalysts) that contained from 0.3 to 0.7 wt-% palladium concentrated near the exterior surface of roughly spherical particles of alumina, which had been heat treated to reduce microporosity. For example, a commercially available catalyst originally available from Mallinckrodt Chemicals, product number E144SDU, containing about 0.5 wt-% Pd on roughly spherical $\frac{1}{16}$" diameter alumina particles, with a surface area of about 40-70 $m^2$/gm and a pore volume of about 0.5 may be used. Similar catalysts commercially available from Engelhard and Calsicat (such as 1435DU) may also be used. Several of the experimental catalysts described below were crushed and then double-screened between 40 and 50 mesh (USS or U.S. sieve series) screens, thus providing catalyst particles with a minimum dimension in the range of from about 0.0117 to about 0.0165 inches. Those skilled in the art will recognize that other known catalysts and supports may likewise be employed without departing from the scope of the invention. Most of the experimental catalysts described below involved dissolving the nitrate salt of the promoter in the amount of water required to just fill the internal pores of the catalyst support, though other techniques as are known in the art may of course be employed.

Example 1

Comparative

Catalyst containing 0.3 wt-% $Pd/Al_2O_3$. A commercially available Engelhard catalyst that contained 0.3 wt-% $Pd/Al_2O_3$ was used for this Example. The alumina supported catalyst particles were roughly spherical and approximately $\frac{1}{16}$ inches in diameter. The catalyst was dried for one hour.

The dried product was reduced in place at 100° C. and 250 psig for two hours with a 2:1 $H_2$:CO gas mixture (66% $H_2$-34% CO).

Example 2

Comparative

Catalyst containing 0.3 wt-% Pd/$Al_2O_3$. Preparation of this catalyst began with the Engelhard catalyst of Example 1 that contained 0.3 wt-% Pd/$Al_2O_3$. The alumina supported catalyst particles were roughly spherical and approximately 1/16 inches in diameter. The catalyst was dried for one hour, crushed and double-screened between 40 and 50 mesh (USS) screens, and reduced in place at 400° C. and 150 psig for one hour with a 2:1 $H_2$:CO gas mixture (66% $H_2$-34% CO).

Example 3

Comparative

Catalyst containing 0.7 wt-% Pd/$Al_2O_3$. Preparation of this catalyst began with an Engelhard catalyst which contained 0.7 wt-% Pd/$Al_2O_3$. The alumina supported catalyst particles were roughly spherical and approximately 1/16 inches in diameter. The catalyst was reduced in place at 50° C. and 250 psig for one hour with a 2:1 $H_2$:CO gas mixture (66% $H_2$-34% CO).

Example 4

Catalyst containing 0.3 wt-% Pd-1.2 wt-% Au/$Al_2O_3$. Preparation of this catalyst began with the Engelhard catalyst of Example 1 that contained 0.3 wt-% Pd/$Al_2O_3$. The alumina supported catalyst particles were roughly spherical and approximately 1/16 inches in diameter. For this Example, the catalyst particles were dropwise impregnated with a gold chloride solution, dried at 150° C. for one hour, and calcined at 300° C. for one hour to produce a 1.2 wt-% Au-0.3 wt-% Pd/$Al_2O_3$ product. The product was crushed and double-screened between 40 and 50 mesh (USS) screens, and reduced in place for one hour at 100° C. and 250 psig with a 2:1 $H_2$:CO gas mixture (66% $H_2$-34% CO).

Example 5

Catalyst containing 0.3 wt-% Pd-0.3 wt-% Ag/$Al_2O_3$. Preparation of this catalyst began with a Calsicat catalyst that contained 0.3 wt-% Pd/$Al_2O_3$. The alumina supported catalyst particles were roughly spherical and approximately 1/16 inches in diameter. For this Example, 10 grams of the Calsicat catalyst was dropwise impregnated with 0.047 grams of $AgNO_3$ dissolved in 5 ml of water, dried for one hour at 150° C., and calcined at 300° C. for one hour to give a 0.3% Ag-0.3% Pd/$Al_2O_3$ product. The product was then crushed and double screened between 40 and 50 mesh (USS) screens and reduced in place at 100° C. and 250 psig for one hour with a 2:1 $H_2$:CO gas mixture (66% $H_2$-34% CO).

Example 6

Catalyst containing 0.3 wt-% Pd-0.6 wt-% Ag/$Al_2O_3$. Preparation of this catalyst began with the Calsicat catalyst of Example 5 that contained 0.3 wt-% Pd/$Al_2O_3$. The alumina supported catalyst particles were roughly spherical and approximately 1/16 inches in diameter. For this Example, the procedure of Example 5 was followed except that the concentration of silver nitrate in the impregnating solution was twice that of Example 5. The product was again dried for one hour at 150° C., and calcined at 300° C. for one hour. The 0.6% Ag-0.3% Pd/$Al_2O_3$ product was then crust and double screened between 40 and 50 mesh (USS) screens, and reduced in place at 100° C. and 250 psig for one hour with a 2:1 $H_2$:CO gas mixture (66% $H_2$-34% CO).

Example 7

Catalyst containing 0.3 wt-% Pd-0.1 wt-% Mn/$Al_2O_3$. This catalyst was prepared from an Engelhard catalyst that contained 0.3 wt-% Pd/$Al_2O_3$. The alumina supported catalyst particles were roughly spherical and approximately 1/16 inches in diameter. For this Example, the catalyst was dropwise impregnated with manganese acetate, dried at 150° C. and calcined at 300° C. to give a 0.3 wt-% Pd-0.1 wt-% Mn/$Al_2O_3$ product. The calcined product was then crushed and double screened between 40 and 50 mesh (USS) screens, and reduced in place at 300° C. and 250 psig for one hour with a 2:1 $H_2$:CO gas mixture (66% $H_2$-34% CO).

Example 8

Catalyst containing 0.3 wt-% Pd-0.385 wt-% In/$Al_2O_3$. This catalyst was prepared from the Engelhard catalyst that contained 0.3 wt-% Pd/$Al_2O_3$. The alumina supported catalyst particles were roughly spherical and approximately 1/16 inches in diameter. For this Example, the catalyst was dropwise impregnated with an aqueous solution of indium nitrate, dried at 150° C. for one hour, and calcined at 300° C. for one hour to give a 0.3 wt-% Pd-0.4 wt-% In/$Al_2O_3$ product. The calcined product was then crushed and double screened between 40 and 50 mesh (USS) screens, and reduced in place at 300-314° C. and 250 psig for one hour with a 2:1 $H_2$:CO gas mixture (66% $H_2$-34% CO).

Example 9

Catalyst containing 0.3 wt-% Pd-0.26 wt-% Ga/$Al_2O_3$. This catalyst was prepared from the Engelhard catalyst that contained 0.3 wt-% Pd/$Al_2O_3$. The alumina supported catalyst particles were roughly spherical and approximately 1/16 inches in diameter. For this Example, the catalyst was dropwise impregnated with an aqueous solution of gallium nitrate, dried at 150° C. for one hour, and calcined at 300° C. for one hour to give 0.3 wt-% Pd-0.26 wt-% Ga/$Al_2O_3$ product. The product was then crushed and double screened between 40 and 50 mesh (USS) screens, and reduced in place at 400° C. and 250 psig for one hour with a 2:1 $H_2$:CO gas mixture (66% $H_2$-34% CO).

Example 10

Catalyst containing 0.5 wt-% Pd-0.5 wt-% Zn/$Al_2O_3$. Preparation of this catalyst began with a palladium catalyst from Calsicat (product number E144SDU) containing 0.5 wt-% Pd/$Al_2O_3$. The alumina supported catalyst particles were roughly spherical and approximately 1/16 inches in diameter. The palladium-containing material was then dropwise impregnated with a solution of zinc formate, dried for one hour at 150° C., and calcined at 300° C. for one hour to give a 0.5 wt-% Pd-0.5 wt-% Zn/$Al_2O_3$ product. The product was then crushed and double screened between 40 and 50 mesh (USS) screens, and reduced in place at 400-420° C. and 250 psig for one hour with a 2:1 $H_2$:CO gas mixture (66% $H_2$-34% CO).

Catalyst Selective Hydrogenation Screening Tests

Example 11

A reaction vessel constructed of one-half inch (OD) stainless steel tube was used for these tests. Approximately 3 $cm^3$ of catalyst was diluted with 6 $cm^3$ of inert low surface area alumina (alundum) as a catalyst surface area diluent, and placed into the reactor in a fixed bed configuration. Other catalyst surface area diluents may of course be used, as will be known to those skilled in the art. The catalyst was placed in the center section of the reactor between two six-inch deep beds of 3 mm glass beads, one placed upstream of the catalyst for preheat purposes and one downstream, in the exit section. A ⅛" diameter thermowell was located near the center of the reactor, thus the reaction temperature was measured near the center of the catalyst bed.

The operating conditions are as shown in Table 1. The liquid reactant flow rate was set at 18 ml/hr of NMP containing 4.2 wt-% dissolved acetylene. A 2:1 $H_2$:CO gas mixture was used and the $H_2/C_2H_2$ ratio was 1.56:1. Product gas analyses (for $C_2$ components only) were obtained after the composition of the product gas, which was taken from a knockout pot that collected virtually all of the NMP, had reached steady state and subsequent samples showed no significant change in composition. The gas composition results are shown in Table 1. The product gas concentrations do not sum to 100% due to the presence of other components in minor amounts and measurement error. Because these were catalyst screening tests, it is estimated that the mass balance closure for these results was about 95%.

For purposes of comparing the performance of the catalyst formulations tested, the selectivity of ethylene to ethane may be estimated by the ratio of the product ethylene concentration to the concentration of ethane, defined here as the screening selectivity $S_s$ (and presented in Table 1) as $S_s=[C_2H_4]/[C_2H_6]$. Also for comparison purposes, the relative acetylene conversions may be estimated from the product acetylene concentrations. This is defined here (and also presented in Table 1) as the screening conversion $S_c=100-[C_2H_2]$ where the acetylene concentration is expressed in percent.

The data shown in Table 1 thus describe representative results for promoted Group VIII selective hydrogenation catalysts made and used in accordance with the invention. As may be seen from examination of the data tabulated in Table 1, significant improvements in the selectivity to ethylene result from the addition of promoters at high acetylene conversion. Contrary to the teachings of the prior art, a progressive decline in activity with time on stream was not observed, and the gallium and indium containing catalysts showed relatively high selectivity. Likewise, excellent selectivity and activity were observed for the catalysts of the invention obtained by applying a promoter metal after first applying the Group VIII metal to the support. Accordingly, the catalysts of the present invention are effective in the selective hydrogenation of acetylene. The indium-promoted catalyst and, to a lesser extent, the gallium-promoted catalyst is effective with palladium on alumina, and exhibit higher selectivity to ethylene than either the silver-promoted or gold-promoted catalysts traditionally used to advantage for the removal of small amounts of acetylene in ethylene by selective hydrogenation in the front-end gas phase hydrogenation process.

TABLE 1

| Catalyst | Composition | T (° C.) | P (psig) | $H_2$/CO Flow (ml/min) | Ethane (%) | Ethylene (%) | Acetylene (%) | $S_s$ | $S_c$ (%) |
|---|---|---|---|---|---|---|---|---|---|
| Example 1 | 0.3% Pd on ¹⁄₁₆" alumina spheres | 111 | 250 | 30 | 10.0 | 89.4 | 0.5 | 8.9 | 99.5 |
| Example 2 | 0.3% Pd on 40-50 mesh alumina particles | 128 | 150 | 35 | 2.6 | 94.0 | 0.80 | 36 | 99.2 |
| Example 3 | 0.7% Pd on ¹⁄₁₆" alumina spheres | 111 | 250 | 40 | 6.4 | 93.4 | 0.1 | 15 | 99.9 |
| Example 4 | 0.3% Pd—1.2% Au on 40-50 mesh alumina particles | 120 | 250 | 35 | 6.25 | 93.50 | 0.15 | 15 | 99.9 |
| Example 2 | 0.3% Pd on 40-50 mesh alumina particles | 119 | 250 | 32 | 2.42 | 91.0 | 6.34 | 38 | 93.7 |
| Example 5 | 0.3% Pd—0.3% Ag on 40-50 mesh alumina particles | 114 | 250 | 30 | 3.68 | 93.5 | 2.77 | 25 | 97.2 |
| Example 6 | 0.3% Pd—0.6% Ag on 40-50 mesh alumina particles | 115 | 250 | 30 | 3.33 | 96.2 | 0.41 | 29 | 99.6 |
| Example 7 | 0.3% Pd—0.1% Mn on 40-50 mesh alumina particles | 122 | 250 | 30 | 3.91 | 95.6 | 0.42 | 24 | 99.6 |
| Example 8 | 0.3% Pd—0.385% In on 40-50 mesh alumina particles | 137 | 250 | 30 | 1.46 | 96.8 | 1.70 | 66 | 98.3 |
| Example 9 | 0.3% Pd—0.26% Ga on 40-50 mesh alumina particles | 130 | 250 | 30 | 2.02 | 97.5 | 0.40 | 48 | 99.6 |

Selective Hydrogenation—Sustained Activity Tests

Example 12

The results obtained from Example 11 and shown in Table 1 were considered promising. Therefore, an extended duration run was made with an indium-containing catalyst similar to that of Example 8 but with 0.22 wt-% indium to determine whether this high selectivity catalyst would also have sustained activity for selective hydrogenation. Operating conditions for the sustained activity tests included: reactor pressure of 150 psig; 1.5 wt-% acetylene was absorbed and dissolved in the NMP absorbent to provide the reactant stream; the molar ratio of $H_2$ to $C_2H_2$ was set at 1.26:1; and the flowrate of reactant through the bed (liquid hourly space velocity) was set to an LHSV of 5 $hr^{-1}$.

The catalyst was operated for about 143 hours, and product gas composition was determined at selected intervals, as shown in Table 2. It is estimated that the mass balance closure for these results was about 95%.

TABLE 2

| Time on Stream (hrs) | 70 | 104 |
|---|---|---|
| Temperature (° C.) | 134 | 134 |
| Pressure (psig) | 150 | 150 |
| Methane (wt-%) | 0.01 | 0.01 |
| Ethane (wt-%) | 1.30 | 1.19 |
| Ethylene (wt-%) | 97.50 | 98.10 |
| Acetylene (wt-%) | 0.39 | 0.08 |
| Trans-2-butene (wt-%) | 0.07 | 0.06 |
| 1-butene (wt-%) | 0.21 | 0.17 |
| Cis-2-butene (wt-%) | 0.07 | 0.06 |
| Butadiene (wt-%) | 0.40 | 0.31 |
| Total (wt-%) | 99.95 | 99.98 |
| $S_s$ | 75 | 82 |
| $S_c$ (%) | 99.6 | 99.9 |

After this extended run, the catalyst bed was flushed with nitrogen at 425° C. and the catalyst was oxidized in air for one hour. The catalyst was then reduced with the 2:1 $H_2$:CO mixture at 417° C. and 150 psig, and tested again to determine whether it was active. The catalyst was again both active and selective for the selective hydrogenation of acetylene dissolved in NMP with a $H_2$ and CO mixture.

Zinc-Promoted Catalyst

Example 13

This example was performed under conditions similar to those of Example 11, using the catalyst prepared as described in Example 10. The reactant stream comprised 1.5 wt-% acetylene in NMP. The $H_2$:CO feed ratio was 2:1 (vol/vol). The $H_2$:$C_2H_2$ to the reactor was 2.76:1. The reaction pressure was maintained at approximately 250 psig and the average temperature in the catalyst bed was 128° C. The reactant stream flowrate was set to a LHSV of 5 $hr^{-1}$.

Table 3 provides results from these tests in the form of product gas composition as a function of reaction time. It is estimated that the mass balance closure for these results was about 98-99%. As will be seen from the results in Table 3, the zinc-promoted catalyst provides improved ethylene selectivity at high acetylene conversion.

The average catalyst bed temperature was 140° C., and the $H_2$:$C_2H_2$ to the reactor was 3.7:1.

The results of this test are provided in Table 4 in the form of gas composition. The gas composition data are the result of gas analyses only; when the $C_4$ compounds that collect in the liquid are combined with those in the gas phase, 3.14 wt-% of the acetylene reacted goes to form $C_4$ compounds initially, but this figure drops to 2.31 wt-% after 14 hours of operation and levels off to about 2.1 wt-% after about 21 hours of operation. It is estimated that the mass balance closure for these results was about 98%-99%.

Accordingly, the progressive decline in activity with time on stream predicted by the conventional art is not observed. Further, the results of Table 3 indicate improvement in selectivity with time on stream for the catalyst of Example 10.

TABLE 4

| Time (hr) | $CH_4$ (wt-%) | $C_2H_6$ (wt-%) | $C_2H_4$ (wt-%) | $C_2H_2$ (wt-%) | $C_4H_8$ (wt-%) | 1,3-$C_4H_8$ (wt-%) | $S_s$ | $S_c$ (%) |
|---|---|---|---|---|---|---|---|---|
| 7 | 0.06 | 0.33 | 97.4 | 1.20 | 0.07 | 0.87 | 295 | 98.8 |
| 14 | 0.07 | 0.60 | 98.1 | 0.68 | 0.10 | 0.43 | 164 | 99.3 |
| 21 | 0.02 | 0.60 | 98.2 | 0.77 | 0.02 | 0.31 | 164 | 99.2 |
| 24 | 0.02 | 0.50 | 98.6 | 0.33 | 0.02 | 0.38 | 197 | 99.7 |

The examples provided in the disclosure are presented for illustration and explanation purposes only and are not intended to limit the claims or embodiment of this invention. While the preferred embodiments of the invention have been shown and described, modification thereof can be made by one skilled in the art without departing from the spirit and teachings of the invention. Process design criteria, pendant processing equipment, and the like for any given implementation of the invention will be readily ascertainable to one of skill in the art based upon the disclosure herein. The embodiments described herein are exemplary only, and are not intended to be limiting. Many variations and modifications of the invention disclosed herein are possible and are within the scope of the invention. Use of the term "optionally" with

TABLE 3

| Time (hr) | $CH_4$ (wt-%) | $C_2H_6$ (wt-%) | $C_2H_4$ (wt-%) | $C_2H_2$ (wt-%) | t-$C_4H_8$ (wt-%) | i-$C_4H_8$ (wt-%) | c-$C_4H_8$ (wt-%) | 1,3-$C_4H_8$ (wt-%) | $S_s$ | $S_c$ (%) |
|---|---|---|---|---|---|---|---|---|---|---|
| 0.5 | 0.04 | 0.91 | 97.4 | 0.48 | 0.04 | 0.09 | 0.07 | 0.85 | 107 | 99.5 |
| 1.0 | 0.02 | 0.87 | 97.4 | 0.37 | 0.05 | 0.09 | 0.08 | 1.00 | 112 | 99.6 |
| 1.5 | 0.02 | 0.85 | 97.5 | 0.29 | 0.05 | 0.09 | 0.07 | 1.00 | 115 | 99.7 |
| 2.0 | 0.01 | 0.84 | 97.6 | 0.24 | 0.04 | 0.09 | 0.07 | 1.00 | 115 | 99.8 |
| 2.5 | 0.01 | 0.83 | 97.7 | 0.21 | 0.04 | 0.08 | 0.06 | 0.97 | 118 | 99.8 |
| 3.0 | 0.01 | 0.82 | 97.8 | 0.20 | 0.04 | 0.08 | 0.06 | 0.93 | 119 | 99.8 |
| 3.5 | 0.01 | 0.81 | 97.9 | 0.18 | 0.04 | 0.07 | 0.06 | 0.89 | 121 | 99.8 |
| 4.0 | 0.01 | 0.81 | 98.0 | 0.16 | 0.03 | 0.07 | 0.05 | 0.83 | 121 | 99.8 |
| 4.5 | 0.01 | 0.80 | 98.1 | 0.14 | 0.03 | 0.07 | 0.05 | 0.77 | 123 | 99.9 |
| 5.0 | 0.01 | 0.79 | 98.2 | 0.12 | 0.03 | 0.06 | 0.04 | 0.72 | 124 | 99.9 |

Sustained Activity—Zinc-Promoted Catalyst

Example 14

This example was again performed using the catalyst of Example 10. The test was performed under conditions similar to those of Example 13 but with the following differences. The reactant stream flowrate was set to a LHSV of 10 $hr^{-1}$.

respect to any element of the invention is intended to mean that the subject element is required, or alternatively, is not required. Both alternatives are intended to be within the scope of the invention.

The discussion of a reference in the Description of the Related Art is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

We claim:

1. A method of making a promoted catalyst for selective hydrogenation comprising:
   impregnating a carrier by incipient wetness impregnation with an aqueous solution of a promoter selected from the group consisting of Group IB metals, Group IIB metals, Group IIIA metals, Group VIIB metals, and combinations thereof, in a concentration sufficient to deposit the promoter on the carrier in a finished concentration of from about 0.05 wt-% to about 1.0 wt-%;
   drying the product of the impregnation for about one hour at about 150° C.;
   calcining the dried product at about 300° C.;
   reducing the calcined product for 1-2 hours at a temperature in the range of from about 100° C. to about 425° C. in an atmosphere consisting of an approximately 2:1 mixture of $H_2$:CO at a pressure of from about 150 psig to about 250 psig.

2. The method of claim 1 wherein the promoter is selected from the group consisting of Group IIIA metals, Group IIB metals, Group VIIB metals, and combinations thereof.

3. The method of claim 2 wherein the promoter is selected from the group consisting of In, Ga, Mn, Zn, and combinations thereof.

4. The method of claim 3 wherein the promoter is Mn or Zn.

5. The method of claim 4 wherein the carrier comprises a Group VIII metal disposed on a support.

6. The method of claim 5 wherein the support comprises particulate alumina.

7. The method of claim 6 wherein the finished concentration of the Group VIII metal is within the range of 0.1 wt-% to 10 wt-%.

8. The method of claim 7 wherein the Group VIII metal is Pd.

9. The method of claim 8 wherein the finished concentration of Pd is within the range of 0.2 wt-% to 0.8 wt-%.

10. The method of claim 9 wherein the finished concentration of Pd is from about 0.2 wt-% to about 0.5 wt-%.

11. The method of claim 9 wherein the promoter is selected from the group consisting of Group IIIA metals, Group IIB metals, Group VIIB metals, and combinations thereof.

12. The method of claim 11 wherein the promoter is selected from the group consisting of Mn, In, Ga, Zn, and combinations thereof.

13. The method of claim 12 wherein the promoter is Mn or Zn.

14. The method of claim 12 wherein the aqueous solution comprises an aqueous solution of the nitrate salt of the promoter, and the reduction is carried out at about 400-420° C. for about one hour.

15. The method of claim 1 wherein the promoter is selected from the group consisting of Group IB metals and combinations thereof, the aqueous solution comprises an aqueous solution of a salt of the promoter, and the reduction is carried out at about 100° C. for about two hours.

16. The method of claim 1 further comprising impregnating the carrier by incipient wetness impregnation with a solution comprising a metal selected from the group consisting of Group VIII metals and combinations thereof, in a concentration sufficient to deposit the metal on the carrier in a finished concentration of from about 0.1 wt-% to about 5.0 wt-%.

17. The method of claim 16 wherein the impregnation steps are performed simultaneously.

18. The method of claim 17 wherein the promoter is selected from the group consisting of Group IIIA metals, Group IIB metals, Group VIIB metals, and combinations thereof.

19. The method of claim 18 wherein the promoter is selected from the group consisting of In, Ga, Mn, Zn, and combinations thereof.

20. The method of claim 19 wherein the promoter is Mn or Zn.

21. The method of claim 19 wherein the carrier comprises alumina.

22. The method of claim 21 wherein the alumina comprises particulate alumina.

23. The method of claim 22 wherein the Group VIII metal is Pd.

24. The method of claim 23 wherein the finished concentration of Pd is from about 0.1 wt-% to about 1.0 wt-%.

25. The method of claim 24 wherein the promoter is selected from the group consisting of Mn, In, Ga, Zn, and combinations thereof.

26. The method of claim 25 wherein the promoter is Mn or Zn.

* * * * *